United States Patent
Kang (10) Patent No.: US 11,541,162 B2
(45) Date of Patent: Jan. 3, 2023

(54) METHOD OF MANAGING MEDICAL SUCTION DEVICE THROUGH NETWORK AND MANAGEMENT SERVER USED FOR THE SAME

(71) Applicant: LMECA CO., LTD., Gangwon-do (KR)

(72) Inventor: Jung-kil Kang, Gyeonggi-do (KR)

(73) Assignee: LMECA CO., LTD., Gangwon-Do (KR)

( * ) Notice: Subject to any disclaimer, the term of this patent is extended or adjusted under 35 U.S.C. 154(b) by 1104 days.

(21) Appl. No.: 16/089,865

(22) PCT Filed: Jul. 14, 2016

(86) PCT No.: PCT/KR2016/007665
§ 371 (c)(1),
(2) Date: Sep. 28, 2018

(87) PCT Pub. No.: WO2017/171149
PCT Pub. Date: Oct. 5, 2017

(65) Prior Publication Data
US 2019/0117859 A1    Apr. 25, 2019

(30) Foreign Application Priority Data
Mar. 29, 2016   (KR) .................. 10-2016-0037431

(51) Int. Cl.
*A61M 1/00*   (2006.01)
*A61B 7/00*   (2006.01)
(Continued)

(52) U.S. Cl.
CPC ............. *A61M 1/74* (2021.05); *A61B 5/0022* (2013.01); *A61B 5/024* (2013.01); *A61B 5/027* (2013.01);
(Continued)

(58) Field of Classification Search
CPC ....... A61B 7/003; A61B 7/04; A61B 5/14539; G06F 13/10; G16H 10/60; G16H 40/63;
(Continued)

(56) References Cited

U.S. PATENT DOCUMENTS

2005/0182355 A1    8/2005   Bui
2009/0050154 A1*   2/2009   Strothmann ........ A61M 16/161
                                                 128/204.23
(Continued)

FOREIGN PATENT DOCUMENTS

JP    2002-311025 A   10/2002
JP    2010-158285 A    7/2010
(Continued)

OTHER PUBLICATIONS

International Search Report for PCT/KR2016/007665 dated Oct. 21, 2016.

*Primary Examiner* — Tuan C Dao
(74) *Attorney, Agent, or Firm* — Novick, Kim & Lee PLLC; Jae Youn Kim (57) ABSTRACT

A method of managing a medical suction device through a network may be embodied by the management server through the steps of: storing operation information of at least one medical suction device in a storage unit provided in the management server, generating an operation start determination reference value of the medical suction device based on the operation information, receiving information on conditions of a patient from a medical suction device installed at an outside, and determining whether to start an operation of the medical suction device that has transmitted the information on conditions of the patient based on the operation start determination reference value and the information on conditions of the patient.

3 Claims, 6 Drawing Sheets

(51) Int. Cl.
*A61B 7/04* (2006.01)
*A61B 5/027* (2006.01)
*A61B 5/024* (2006.01)
*A61B 5/091* (2006.01)
*A61B 5/145* (2006.01)
*A61B 5/00* (2006.01)
*G16H 40/67* (2018.01)
*G06F 13/10* (2006.01)
*G16H 40/60* (2018.01)
*G16H 40/63* (2018.01)

(52) U.S. Cl.
CPC .............. *A61B 5/091* (2013.01); *A61B 5/145* (2013.01); *A61B 7/003* (2013.01); *A61B 7/04* (2013.01); *G06F 13/10* (2013.01); *G16H 40/60* (2018.01); *G16H 40/63* (2018.01); *G16H 40/67* (2018.01); *A61M 2205/3375* (2013.01); *A61M 2205/3561* (2013.01); *A61M 2205/50* (2013.01); *A61M 2210/1025* (2013.01); *A61M 2230/06* (2013.01); *A61M 2230/205* (2013.01); *A61M 2230/40* (2013.01)

(58) Field of Classification Search
CPC .......... G16H 40/67; A61M 2205/3375; A61M 2205/3561; A61M 2205/50; A61M 2210/1025; A61M 2230/06; A61M 2230/205; A61M 2230/40; G06Q 50/10; G06Q 50/22
See application file for complete search history.

(56) References Cited

U.S. PATENT DOCUMENTS

| | | | | |
|---|---|---|---|---|
| 2010/0057046 | A1* | 3/2010 | Stevens | A61M 16/0051 128/204.23 |
| 2012/0272955 | A1* | 11/2012 | Cool | A61M 16/024 128/207.14 |
| 2013/0053719 | A1* | 2/2013 | Wekell | A61M 15/008 600/538 |
| 2013/0324954 | A1 | 12/2013 | Friedrich et al. | |
| 2013/0333695 | A1* | 12/2013 | Dellaca | A61M 15/009 128/200.14 |
| 2015/0034082 | A1* | 2/2015 | Kimm | A61B 5/14542 128/202.16 |
| 2015/0034085 | A1* | 2/2015 | Klein | A61M 16/122 128/203.14 |
| 2016/0144141 | A1* | 5/2016 | Biswas | A61M 15/009 128/200.23 |
| 2016/0263333 | A1* | 9/2016 | Dellaca | A61M 16/14 |

FOREIGN PATENT DOCUMENTS

| | | |
|---|---|---|
| KR | 10-2014-0126933 A | 11/2014 |
| KR | 10-2015-0130108 A | 11/2015 |
| WO | WO 2015/130007 A1 | 9/2015 |

* cited by examiner

METHOD OF MANAGING MEDICAL SUCTION DEVICE THROUGH NETWORK AND MANAGEMENT SERVER USED FOR THE SAME

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2016/007665, filed Jul. 14, 2016, which claims priority to the benefit of Korean Patent Application No. 10-2016-0037431 filed in the Korean Intellectual Property Office on Mar. 29, 2016, the entire contents of which are incorporated herein by reference.

TECHNICAL FIELD

The present invention relates to a method of managing a medical suction device through a network and a management server used for the same, and more specifically, to a method of managing a medical suction device through a network, which controls medical suction devices installed at a plurality of places through a management server that has analysis values for accumulated information on operation data of the medical suction devices, such that it is possible to secure an accurate operation of the medical suction devices, and timeliness of a relief measure for patients, and the management server used for the same.

BACKGROUND ART

A medical suction device is a medical foreign material suction device which sucks in and removes by force into a container foreign materials such as blood, saliva, vomitus and secreta that are generated from an inside of patient's body while operating on the patient in hospitals.

In general, patients with impaired mobility at home or hospital have a suction device mounted constantly for a guardian or nurse to drain foreign material out of the trachea or bronchial tubes.

However, since foreign materials may be generated during sleep to block the trachea, the nurse, carer or guardian should operate the suction device from time to time. In addition, these guardians have to constantly check the condition of the patient at all times, as well as have the difficulty of removing foreign matters by driving the suction device from time to time.

Furthermore, in the prior art, it is necessary to grasp the condition of the patient according to a skill level of a person who cares for the patient, and to take appropriate relief measures through the medical suction device according to the condition of the patient. Since a success of the relief for the patient is determined by an execution of appropriate measures, when a nursing staff is inattentive or inexperienced, the patient may be in an emergency state, for example, a patient's airway becomes obstructed due to foreign matters, and serious problems may occur if left unattended.

SUMMARY

Accordingly, it is an object of the present invention to provide a method of managing a medical suction device through a network, which controls medical suction devices installed at a plurality of places through a management server that has analysis values for accumulated information on operation data of the medical suction devices, such that it is possible to secure an accurate operation of the medical suction devices, and timeliness of a relief measure for patients, and the management server used for the same.

To achieve the above object, a management server according to an aspect of the present invention includes: a storage unit configured to store operation information of at least one medical suction device; a generation unit configured to generate an operation start determination reference value of the medical suction device based on the operation information; a reception unit configured to receive information on conditions of a patient from a medical suction device installed at an outside; and a determination unit configured to determine whether to start an operation of the medical suction device that has transmitted the information on conditions of the patient based on the operation start determination reference value and the information on conditions of the patient.

Meanwhile, a method of managing a medical suction device through a network according to another aspect of the present invention includes: (a) storing, by a management server, operation information of at least one medical suction device in a storage unit provided in the management server; (b) generating, by the management server, an operation start determination reference value of the medical suction device based on the operation information; (c) receiving, by the management server, information on conditions of a patient from a medical suction device installed at an outside; and (d) determining, by the management server, whether to start the operation of the medical suction device that has transmitted the information on conditions of the patient based on the operation start determination reference value and the information on conditions of the patient.

Further, a recording medium according to another aspect of the present invention includes a program recorded thereon to execute the above method.

According to the present invention, the medical suction devices installed at a plurality of places are controlled through the management server that has analysis values for accumulated information on operation data of the medical suction devices, such that it is possible to secure an accurate operation of the medical suction devices, and timeliness of a relief measure for patients.

DETAILED DESCRIPTION

Hereinafter, the present invention will be described in detail with reference to the accompanying drawings. Referring to the drawings, wherein like reference characters designate like or corresponding parts throughout the several views. In the embodiments of the present invention, the publicly known functions and configurations that are judged to be able to make the purport of the present invention unnecessarily obscure will not be described.

Figure 1:
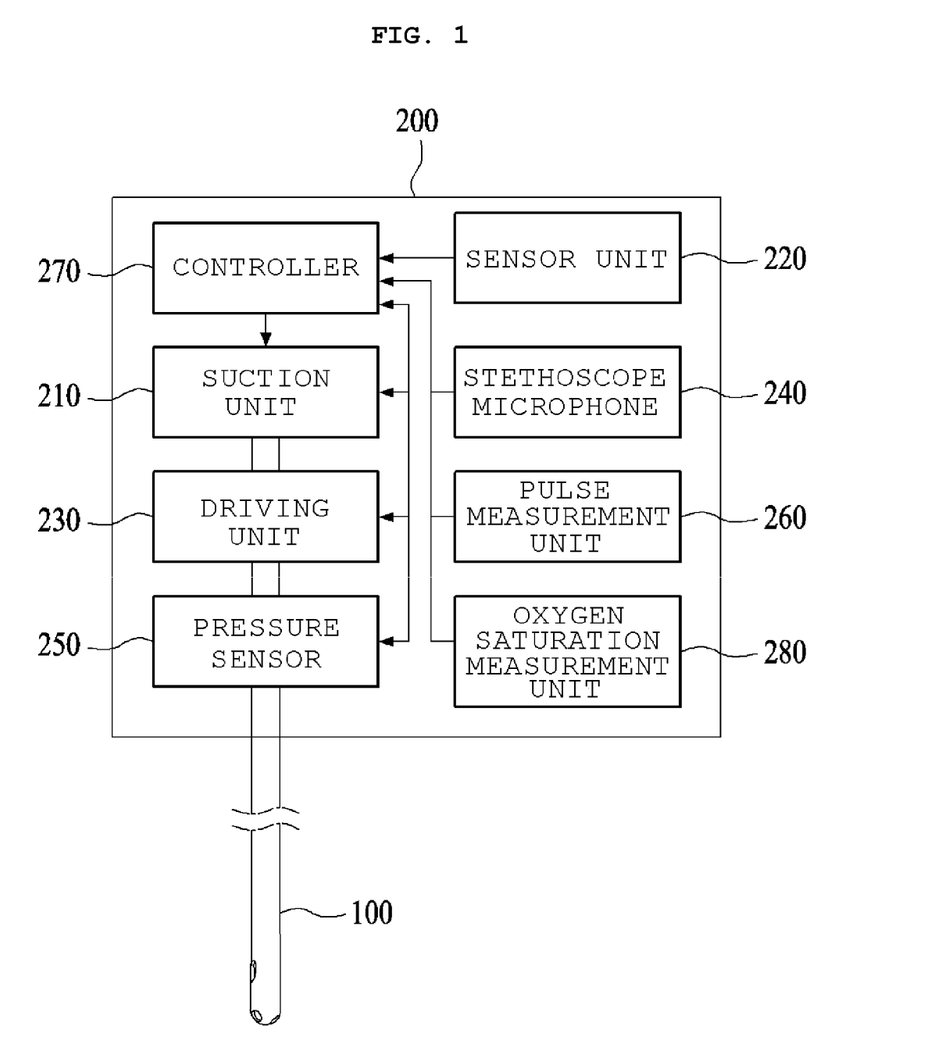
FIG. 1 is a block diagram illustrating a structure of a medical suction device according to an embodiment of the present invention.

FIG. 1 is a block diagram illustrating a structure of a medical suction device according to an embodiment of the present invention. A medical suction device 200 according to the embodiment of the present invention performs a function of removing foreign matters in a respiratory organ of a patient using a catheter 100. To this end, the medical suction device includes a suction pump 210 installed by connecting to one end of the catheter 100, a sensor unit 220, a driving unit 230, a stethoscope microphone 240, a pressure sensor 250, a pulse measurement unit 260, a controller 270, and an oxygen saturation measurement unit 280.

First, the suction pump 210 is installed at one end of the catheter 100, and generates a suction pressure inside the catheter 100 so that foreign matters such as sputum are sucked through the other end of the catheter 100 with being inserted into the respiratory organ of the patient.

The sensor unit 220 includes a mass flow meter (MFM) sensor for measuring masses of inspiratory gas and exhalatory gas of the patient, respectively, and performs a function of measuring the masses of inspiratory gas and exhalatory gas of the patient and transmitting the measured results to the controller 270.

Meanwhile, the driving unit 230 moves the catheter 100 forward to insert the catheter 100 into bronchial tubes, or moves the catheter 100 backward to remove the catheter 100 from the bronchial tubes.

The stethoscope microphone 240 measures auscultatory sounds of the patient and transmits the measured auscultatory sounds to the controller 270. The pulse measurement unit 260 measures a pulse rate of the patient and transmits the measured pulse rate to the controller 270. The oxygen saturation measurement unit 280 measures an oxidation saturation from a blood sample collected from the patient and transmits the measured oxygen saturation to the controller 270.

Meanwhile, the controller 270 performs a function of determining whether it is necessary to remove foreign matters such as sputum in the bronchial tubes of the patient based on information on conditions of the patient including information on auscultatory sounds of the patient received from the stethoscope microphone 240, information on pulse rates of the patient received from the pulse measurement unit 260, and information on oxygen saturations of the patient received from the oxygen saturation measurement unit 280.

In addition, the pressure sensor 250 measures a pressure (negative pressure) formed inside the catheter 100, and transmits the measured pressure value to the controller 270.

Figure 2:
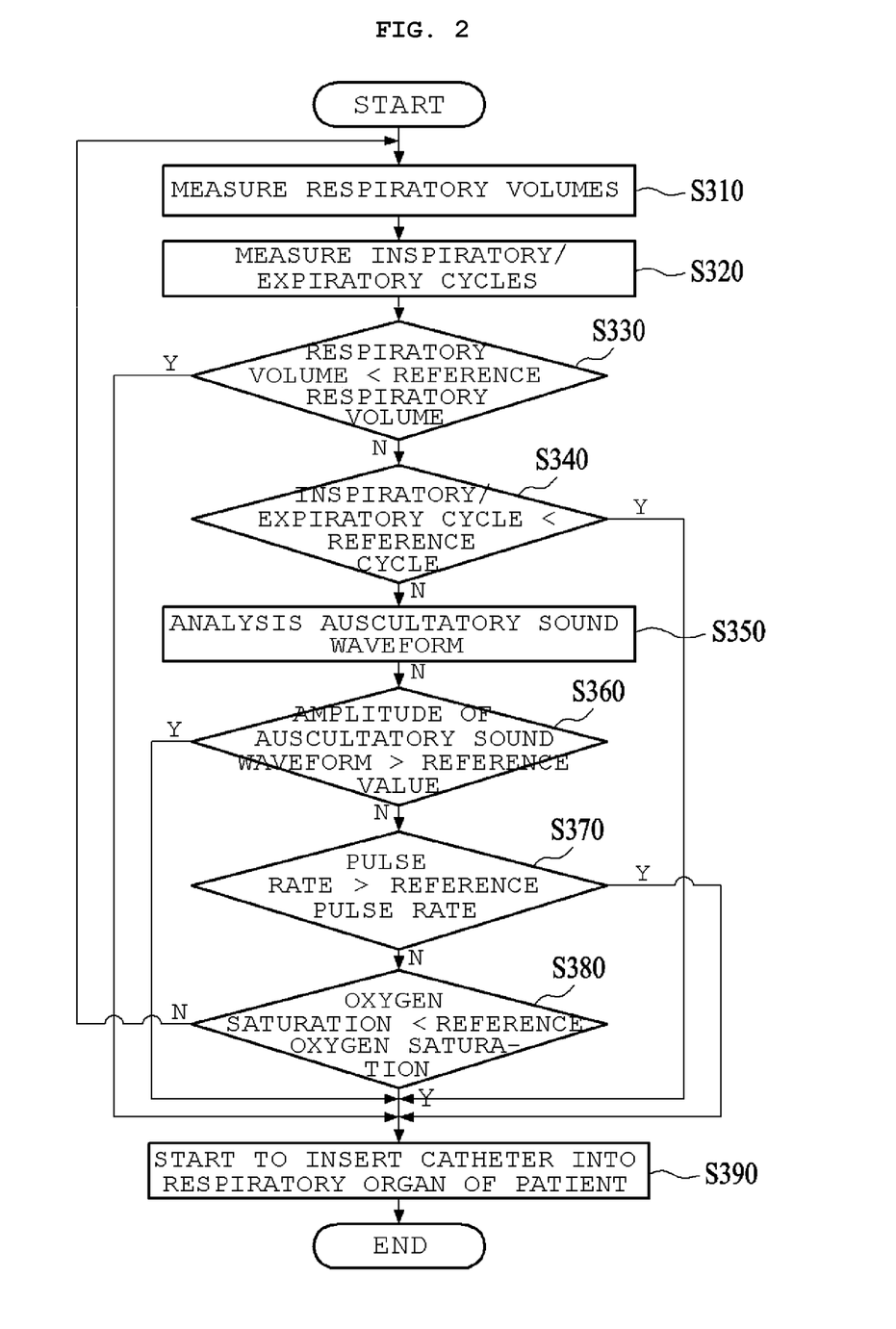
FIG. 2 is a flowchart illustrating a procedure and steps for executing a method of controlling the medical suction device according to the embodiment of the present invention.

FIG. 2 is a flowchart illustrating a procedure and steps for executing a method of controlling the medical suction device 200 according to the embodiment of the present invention. Hereinafter, the steps for executing the method of controlling the medical suction device 200 according to the embodiment of the present invention will be described with reference to FIGS. 1 and 2.

First, the sensor unit 220 includes a first mass flow meter sensor and a second mass flow meter sensor. The first mass flow meter sensor measures an expiratory tidal volume of the patient from an expiratory outlet port of a respiratory mask worn by the patient and the second mass flow meter sensor measures an inspiratory tidal volume of the patient from an inspiratory inlet port of the respiratory mask.

Meanwhile, the controller 270 alternately receives the measured value of the expiratory tidal volume of the patient from the first mass flow meter sensor and the measured value of the inspiratory tidal volume of the patient from the second mass flow meter sensor. As a result, the controller 270 can secure and determine information on tidal volumes per respiratory cycle of the patient in real time based on the measured values received from the first and second mass flow meter sensors.

In addition, the controller 270 calculates an interval between the time when the measured value of the expiratory tidal volume is received from the first mass flow meter sensor and the time when the measured value of the next expiratory tidal volume is received, thereby measuring the respiratory (inspiratory/expiratory) cycle of the patient (S320).

As described above, the information on respiratory volumes of the patient and information on the respiratory cycles of the patient are accumulated and stored in the controller 270 in real time. The controller 270 calculates and stores a cumulative average value of the respiratory volumes of the patient based on such information, and calculates and stores a cumulative average value of the respiratory cycles of the patient.

Meanwhile, the controller 270 determines whether the tidal volumes per respiratory cycle of the patient received from the sensor unit 220 in real time is less than a cumulative average value of the respiratory volumes ('reference respiratory volume') of the patient (S330).

In general, when the foreign matters such as sputum are accumulated in the respiratory organ at a predetermined level or more, the patient's breathing becomes challenging. As a result, the respiratory cycle is shortened and the tidal volumes per respiratory cycle are reduced.

Accordingly, when it is determined by the controller 270 that the tidal volume per respiratory cycle of the patient is less than the cumulative average value of the respiratory volumes (reference respiratory volume) of the patient, the controller 270 determines that it is necessary to remove the sputum from the patient, and transmits operation start commands to the suction pump 210 and the driving unit 230. Thereby, the catheter 100 starts to be inserted into the respiratory organ of the patient (S390).

Meanwhile, in the above-described step S330, if it is determined that the tidal volume per respiratory cycle of the patient is the cumulative average value of the respiratory volumes (reference respiratory volume) or more of the patient, the controller 270 determines whether the current respiratory cycle of the patient is smaller than a cumulative average value of the respiratory cycles ('reference cycle') of the patient (S340).

As a result, when it is determined that the current respiratory cycle measured from the patient is smaller than the cumulative average value of the respiratory cycles (reference cycle), although there is no abnormality in the respiratory volume of the patient, the controller determines that the respiration becomes faster due to the sputum or the like, and transmits operation start commands to the suction pump 210 and the driving unit 230. Thereby, the catheter 100 starts to be inserted into the respiratory organ of the patient (S390).

Meanwhile, in the above-described step S340, if it is determined by the controller 270 that the current respiratory cycle measured from the patient is not shorter than the cumulative average value of the respiratory cycles (reference cycle), the controller 270 analyzes waveforms of the auscultatory sounds of the patient, and determines whether a maximum amplitude of the analyzed waveforms exceeds a predetermined reference amplitude value (S360).

Figure 3:
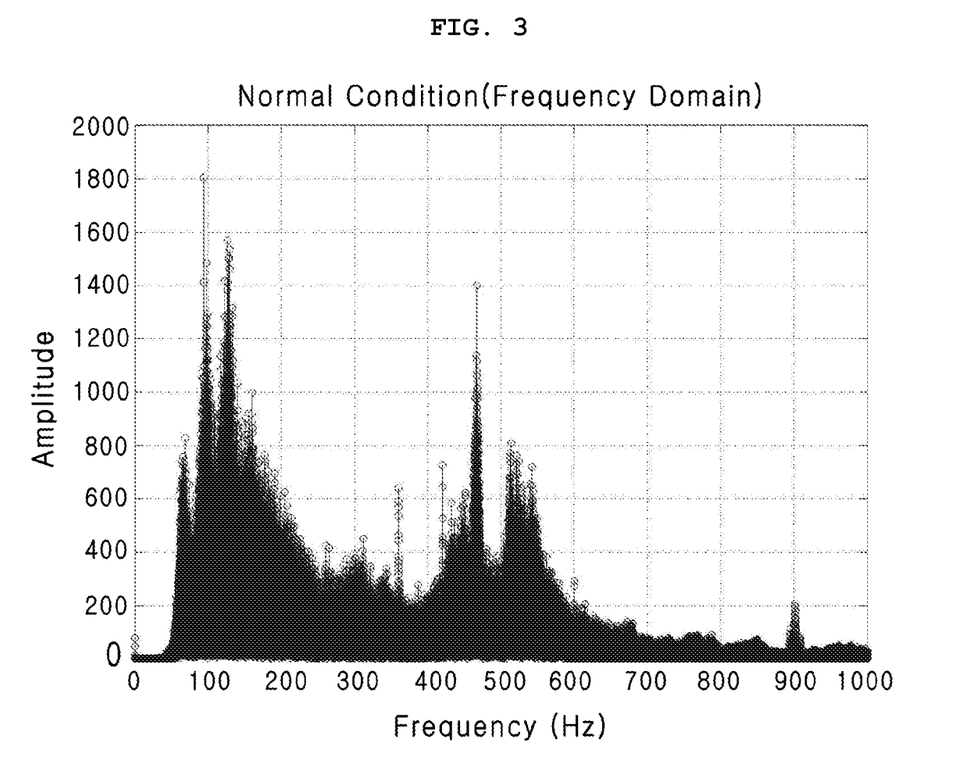
FIG. 3 is a graph illustrating waveforms of auscultatory sounds measured from a patient without respiratory disturbance due to sputum or the like with being converted into a frequency domain.

In particular, the controller 270 normally receives the auscultatory sounds (or the sound of breathing) from the patient's chest measured from the stethoscope microphone 240 in real time, and performs an analysis of the waveforms as illustrated in FIG. 3 for the received auscultatory sounds. FIG. 3 is a graph illustrating the waveforms of auscultatory sounds measured from the patient without respiratory disturbance caused by the sputum or the like with being converted into a frequency domain.

The controller 270 sets an average value obtained by accumulating the maximum amplitudes of the analyzed waveforms for the auscultatory sounds received from the stethoscope microphone in real time as a reference amplitude value.

Meanwhile, the controller 270 analyzes the auscultatory sounds received from the stethoscope microphone 240. At this time, if it is determined that the maximum amplitude of the analyzed waveforms exceeds the predetermined reference amplitude value, the controller 270 determines that the patient's breathing is irregular due to the sputum or the like, and transmits operation start commands to the suction pump 210 and the driving unit 230. Thereby, the catheter 100 starts to be inserted into the respiratory organ of the patient (S390).

Figure 4:
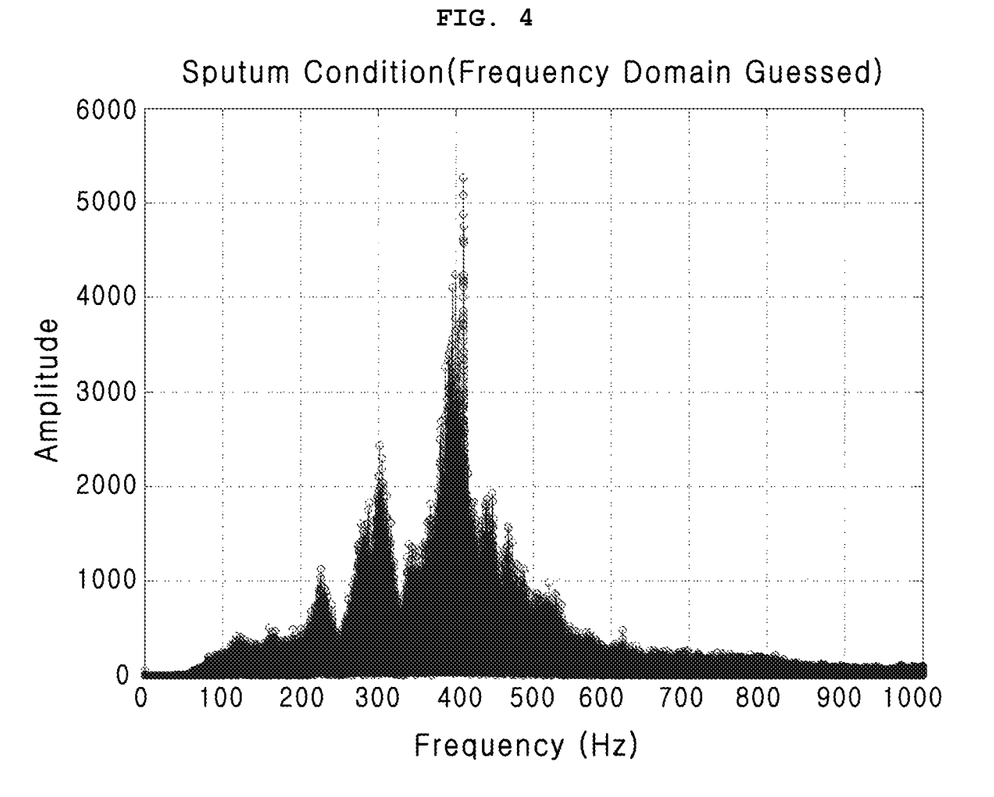
FIG. 4 is a graph illustrating waveforms of auscultatory sounds measured from a patient suffering from the respiratory disturbance due to the sputum or the like with being converted into a frequency domain.

Specifically, as illustrated in FIG. 4, it can be seen that the maximum amplitude of the waveforms of the auscultatory sounds measured from the patient having respiratory disturbance due to the sputum or the like exceeds the maximum amplitude of the waveforms in a normal state from FIG. 3.

Meanwhile, in the above-described step S360, if it is determined by the controller 270 that the maximum amplitude of the waveforms analyzed for the auscultatory sounds received from the stethoscope microphone 240 does not exceed the predetermined reference amplitude value, the controller 270 determines whether the current pulse rate of the patient exceeds a reference pulse rate (S370).

Specifically, the controller 270 normally receives the pulse rates of the patient in real time from the pulse measurement unit 260 mounted on the patient's wrist, and sets an average value of the received cumulative pulse rates as the reference pulse rate.

Meanwhile, if it is determined by the controller 270 that the pulse rate received from the pulse measurement unit 260 exceeds the reference pulse rate, the controller 270 determines that an unconscious patient has difficulty in breathing due to the foreign matters such as sputum in the respiratory organ, consequently the pulse rate of the patient is increased, and transmits operation start commands to the suction pump 210 and the driving unit 230. Thereby, the catheter 100 starts to be inserted into the respiratory organ of the patient (S390).

Meanwhile, in the above-described step S370, if it is determined by the controller 270 that the pulse rate received from the pulse measurement unit 260 does not exceed the reference pulse rate, the controller 270 determines whether the current oxygen saturation measured from the patient is less than a reference oxygen saturation which corresponds to about 80% of the oxygen saturation in the normal state (S380).

Meanwhile, when it is determined by the controller 270 that the current oxygen saturation of the patient received from the oxygen saturation measurement unit 280 is less than the reference oxygen saturation, the controller 270 determines that the unconscious patient has difficulty in breathing due to the foreign matters such as sputum in the respiratory organ, consequently the oxygen saturation of the patient is decreased, and transmits operation start commands to the suction pump 210 and the driving unit 230. Thereby, the catheter 100 starts to be inserted into the respiratory organ of the patient (S390).

Meanwhile, to embody the present invention, when the controller 270 transmits the operation start commands to the suction pump 210 and the driving unit 230, it is preferable that the information on conditions of the patient is stored in a separate memory provided in the medical suction device 200.

The information on conditions of the patient determined by the controller 270 as an operation start condition of the medical suction device 200 will be referred to as 'operation start information' in the present disclosure. The operation start information includes the information on the respiratory volumes of the patient, information on the respiratory (inspiratory/expiratory) cycles, information on the maximum amplitude values of the auscultatory sound waveforms, information on the pulse rates, and information on the oxygen saturations.

Meanwhile, pieces of such operation start information are individually stored in each of the medical suction devices 200. Therefore, the inventor of the present invention has conceived a method of managing the medical suction device through a network by utilizing the operation start information individually stored in a plurality of medical suction devices 200, and has completed the present invention based on the method.

Figure 5:
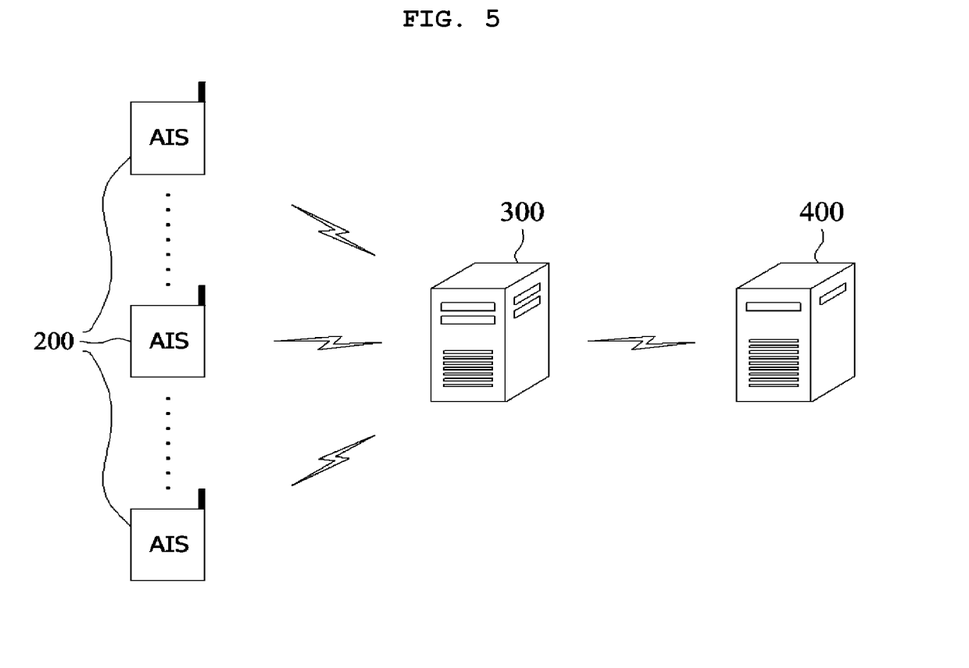
FIG. 5 is a schematic view illustrating a configuration of a management system of a medical suction device through a network according to the present invention.

FIG. 5 is a schematic view illustrating a configuration of a management system of a medical suction device 200 through a network according to the present invention. Referring to FIG. 5, the management system of the medical suction device 200 through the network according to the present invention includes a plurality of medical suction devices 200, a management server 300, and a hospital server 400.

The plurality of medical suction devices 200 are installed in each of a plurality of sick rooms in the hospital or are installed in each of a plurality of hospitals, and are provided with a separate communication module so as to enable wireless communication with the management server 300.

The management server 300 receives and stores the operation start information from the plurality of medical suction devices 200 which are installed in a plurality of places and independently operated, generates an operation start determination reference value of the medical suction devices 200 based on the accumulated operation start information, and determines whether an operation of the medical suction devices 200 is started based on the information on conditions of the patient (information on the respiratory volumes and the respiratory cycles, and information on the auscultatory sound waveforms, pulse rates and oxygen saturations) received from the medical suction device 200 and the operation start determination reference value.

The hospital server 400 is a server installed in a hospital in which the plurality of medical suction devices 200 are installed and operated, and is configured to receive an operation start determination reference value from the management server 300, and determine whether an operation of the medical suction devices 200 is started based on the received operation start determination reference value.

Figure 6:
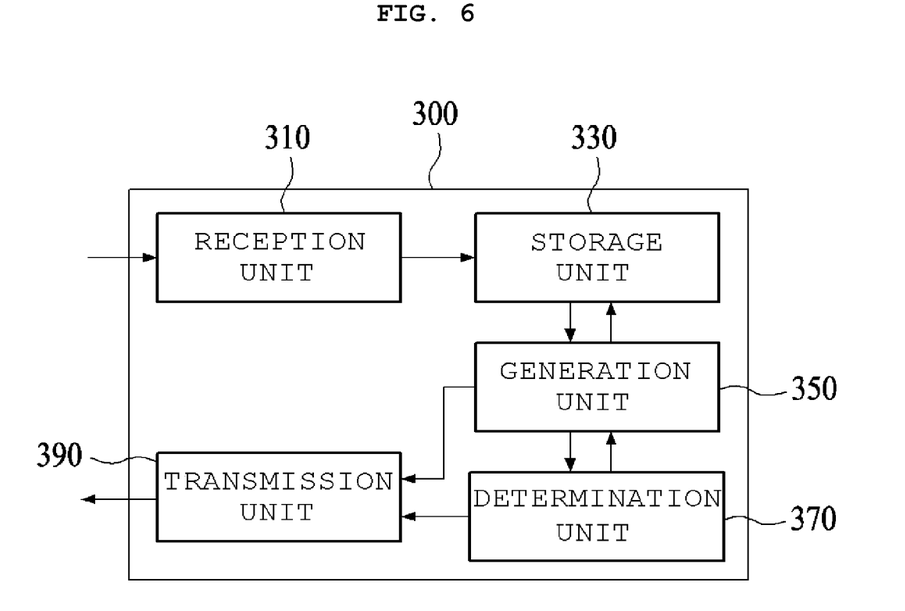
FIG. 6 is a block diagram illustrating the structure and function of a management server included in the management system of the medical suction device through a network according to the present invention.

FIG. 6 is a block diagram illustrating the structure and function of a management server 300 included in the management system of the medical suction device 200 through a network according to the present invention. Referring to FIG. 6, the management server 300 in the management system of the medical suction device 200 through a network according to the present invention includes a reception unit 310, a storage unit 330, a generation unit 350, a determination unit 370, and a transmission unit 390.

First, the reception unit 310 of the management server 300 receives the operation start information from the plurality of medical suction devices 200, and the storage unit 330 stores the operation start information received from the plurality of medical suction devices 200.

The generation unit 350 of the management server 300 generates an operation start determination reference value of the medical suction device 200 based on the operation start information stored in the storage unit 330. The determination unit 370 performs a function of determining whether an operation of the medical suction device 200 installed for the patient is started based on the operation start determination reference value of the medical suction device 200 and the information on conditions of the patient.

Meanwhile, the transmission unit 390 of the management server 300 performs a function of transmitting the operation start command according to the operation start determination of the determination unit 370 to the medical suction device 200.

Figure 7:
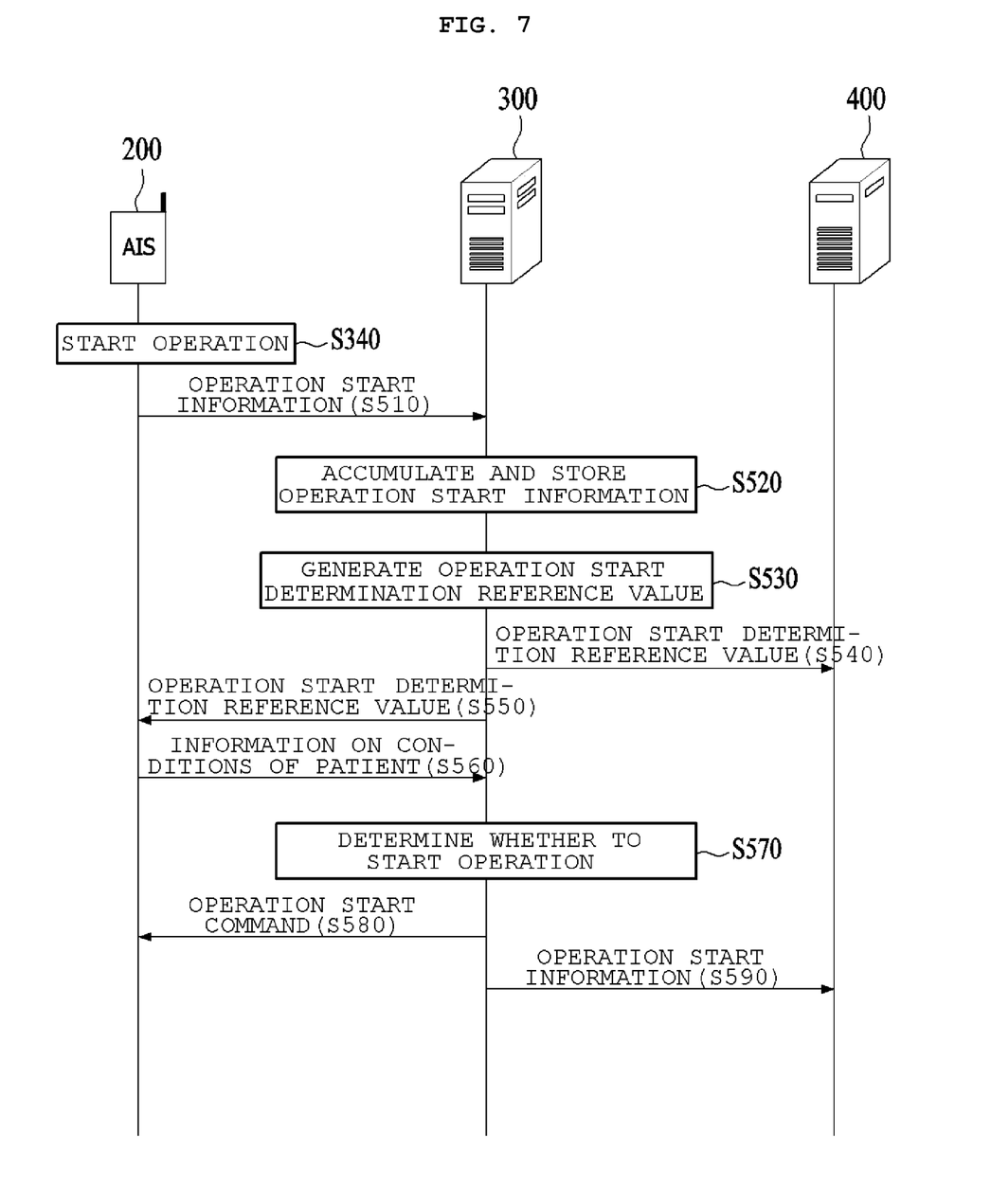
FIG. 7 is a flowchart illustrating steps and signal transmission for executing a method of managing a medical suction device through a network according to the present invention.

FIG. 7 is a flowchart illustrating steps and signal transmission for executing a method of managing the medical suction device 200 through a network according to the present invention. Hereinafter, the steps for executing the method of managing the medical suction device 200 through a network according to the embodiment of the present invention will be described with reference to FIGS. 5 to 7.

First, the medical suction device 200 starts to operate by executing the control method of the medical suction device 200 as described in FIG. 2 (S500), and the medical suction device 200 transmits operation start information at the time of starting the operation to the management server 300 (S510).

As described above, the reception unit 310 of the management server 300 receives the respective operation start information from the medical suction devices 200 installed at the plurality of places, and the received operation start information is accumulated and stored in the storage unit 330 of the management server 300 (S520).

The generation unit 350 of the management server 300 generates an operation start determination reference value using the operation start information cumulatively stored in the storage unit 330 (S530), and the generated operation start determination reference value is stored in the storage unit 330 of the management server 300.

Specifically, the generation unit 350 of the management server 300 generates: a respiratory volume reference value using the cumulative average value of the respiratory volumes; a respiratory cycle reference value using the cumulative average value of respiratory (inspiratory/exhalatory) cycles; an auscultatory sound waveform reference value using the cumulative average value of the maximum amplitude values of the auscultatory sound waveforms; a pulse rate reference value using the cumulative average value of the pulse rates; and an oxygen saturation reference value using the cumulative average value of the oxygen saturations, among the operation start information cumulatively stored in the storage unit 330.

As described above, the respiratory volume reference value, respiratory cycle reference value, auscultatory sound waveform reference value, pulse rate reference value, and oxygen saturation reference value generated by the generation unit 350 are stored in the storage unit 330 of the management server 300 as the operation start determination reference value of the medical suction device 200.

Meanwhile, the transmission unit 390 of the management server 300 transmits the operation start determination reference value generated in the above-described step S530 to the hospital server 400 (S540). Therefore, the hospital server 400 may be configured so as to independently manage and control the medical suction devices 200 installed in the hospital based on the operation start determination reference values transmitted by the transmission unit.

In addition, the transmission unit 390 of the management server 300 may transmit the operation start determination reference values generated in the above-described step S530 to each of the medical suction devices 200 (S540). Thereby, the medical suction devices 200 may determine whether an insertion operation of the catheter into the respiratory organ of the patient is started based on the operation start determination reference values generated on the basis of the operation start information collected from the various medical suction devices 200, such that an occurrence of error can be minimized at the time of determining whether to start the operation.

Further, when determining whether to start the operation, the medical suction device 200 may transmit the information on conditions of the patient in the hospital in which the medical suction device 200 is installed to the management server 300 in order to request a more accurate determination (S560).

Accordingly, the reception unit 310 of the management server 300 receives the information on conditions of the patient from the medical suction device 200, and the determination unit 370 of the management server 300 determines whether the operation of the medical suction device 200 is started based on the operation start determination reference value stored in the storage unit and the information on conditions of the patient (S570).

Specifically, the determination unit 370 of the management server 300 may determine whether the operation of the medical suction device 200 is started in the cases in which: the information on the respiratory volumes of the patient is less than the respiratory volume reference value; the respiratory cycle of the patient is shorter than the respiratory cycle reference value; the maximum amplitude in the auscultatory sound waveforms of the patient exceeds the auscultatory sound waveform reference value; the pulse rate of the patient exceeds the pulse rate reference value; or the oxygen saturation of the patient is less than the oxygen saturation reference value, among the information on conditions of the patient.

When determining the start of the operation of the medical suction device 200 by the determination unit 370 of the management server 300, the transmission unit 390 of the management server 300 transmits an operation start command to the medical suction device 200 that has transmitted the information on conditions of the patient from the management server 300 in the above-described step S560 (S580).

Thereby, the medical suction device 200 receives the operation start command from the management server 300, and then the medical suction device 200 starts an operation to insert the catheter into the respiratory organ of the patient.

Meanwhile, the management server 300 that has transmitted the operation start command to the medical suction device 200 in the above-described step S580 may transmit the information on conditions of the patient, which is based on the determination of whether the operation of the medical suction device 200 is started, to the hospital server 400. Thereby, the hospital may be able to immediately perform a coordinated care service for the patient (S590).

Terms used in the present application are used only to describe specific embodiments, and are not intended to limit the present invention. Singular expressions used herein include plural expressions unless they have definitely opposite meanings in the context. In the present application, it should be understood that term "include" or "have" indicates that a feature, a number, a step, an operation, a component, a part or the combination thereof described in the specification is present, but does not exclude a possibility of presence or addition of one or more other features, numbers, steps, operations, components, parts or combinations thereof, in advance.

While the present invention has been described with reference to the preferred embodiments and modified examples, the present invention is not limited to the above-described specific embodiments and the modified examples, and it will be understood by those skilled in the related art that various modifications and variations may be made therein without departing from the scope of the present invention as defined by the appended claims, as well as these modifications and variations should not be understood separately from the technical spirit and prospect of the present invention.

The present invention can be applied to the medical suction device, such that industrial applicability thereof may be recognized in the medical device industrial fields.

The invention claimed is:

1. A management system of a medical suction device through a network, the management system comprising a management server configured to:
   store operation information of the medical suction device;
   generate an operation start determination reference value of the medical suction device based on the operation information;
   receive information on conditions of a patient from the medical suction device; and
   determine whether to start an operation of the medical suction device that has transmitted the information on conditions of the patient based on the operation start determination reference value and the information on conditions of the patient,
   wherein the medical suction device comprises:
   a catheter;
   a suction pump disposed at one end of the catheter to generate a suction pressure inside the catheter;
   a sensor configured to measure masses of inspiratory gas and exhalatory gas of the patient;
   a driving unit configured to move the catheter forward to insert the catheter into a respiratory organ of the patient;
   a stethoscope microphone configured to measure auscultatory sounds of the patient; and
   a controller configured to:
   determine whether a tidal volume per respiratory cycle of the patient is less than a reference respiratory volume, and control the catheter to start to be inserted into the respiratory organ of the patient if it is determined that the tidal volume per respiratory cycle of the patient is less than the reference respiratory volume;
   if it is determined that the tidal volume per respiratory cycle of the patient is greater than or equal to the reference respiratory volume, determine whether a respiratory cycle of the patient is less than a reference cycle, and control the catheter to start to be inserted into the respiratory organ of the patient if it is determined that the respiratory cycle of the patient is less than the reference cycle; and
   if it is determined that the respiratory cycle of the patient is greater than or equal to the reference cycle, determine whether a maximum amplitude of waveforms of the auscultatory sounds of the patient exceeds a reference amplitude value, and control the catheter to start to be inserted into the respiratory organ of the patient if it is determined that the maximum amplitude of waveforms of the auscultatory sounds of the patient exceeds the reference amplitude value.

2. A method of managing a medical suction device through a network, the method comprising:
   (a) storing, by a management server, operation information of the medical suction device in a storage unit provided in the management server;
   (b) generating, by the management server, an operation start determination reference value of the medical suction device based on the operation information;
   (c) receiving, by the management server, information on conditions of a patient from a the medical suction device; and
   (d) determining, by the management server, whether to start the operation of the medical suction device that has transmitted the information on conditions of the patient based on the operation start determination reference value and the information on conditions of the patient,
   wherein the medical suction device comprises:
   a catheter;
   a suction pump disposed at one end of the catheter to generate a suction pressure inside the catheter;
   a sensor configured to measure masses of inspiratory gas and exhalatory gas of the patient;
   a driving unit configured to move the catheter forward to insert the catheter into a respiratory organ of the patient;
   a stethoscope microphone configured to measure auscultatory sounds of the patient; and
   a controller configured to:
   determine whether a tidal volume per respiratory cycle of the patient is less than a reference respiratory volume, and control the catheter to start to be inserted into the respiratory organ of the patient if it is determined that the tidal volume per respiratory cycle of the patient is less than the reference respiratory volume;
   if it is determined that the tidal volume per respiratory cycle of the patient is greater than or equal to the reference respiratory volume, determine whether a respiratory cycle of the patient is less than a reference cycle, and control the catheter to start to be inserted into the respiratory organ of the patient if it is determined that the respiratory cycle of the patient is less than the reference cycle; and
   if it is determined that the respiratory cycle of the patient is greater than or equal to the reference cycle, determine whether a maximum amplitude of waveforms of the auscultatory sounds of the patient exceeds a reference amplitude value, and control the catheter to start to be inserted into the respiratory organ of the patient if it is determined that the maximum amplitude of waveforms of the auscultatory sounds of the patient exceeds the reference amplitude value.

3. A non-transitory computer-readable storage medium having a computer program recorded thereon to execute the method according to claim 2, when the computer program is run by a computer.

* * * * *